United States Patent [19]

Kammann, Jr. et al.

[11] 4,380,498

[45] Apr. 19, 1983

[54] SULFURIZED, TRANSESTERIFIED OIL ADDITIVES AND THEIR USE IN A LUBRICATING OIL AND A FUEL

[75] Inventors: Karl P. Kammann, Jr., Crown Point, Ind.; Marvin J. Den Herder, Olympia Fields; Terrence L. Wagner, Crete Township, Will County, both of Ill.

[73] Assignee: Ferro Corporation, Cleveland, Ohio

[21] Appl. No.: 291,544

[22] Filed: Aug. 10, 1981

[51] Int. Cl.$^3$ .................. C10M 1/20; C10M 1/38; C10L 1/18; C10L 1/24
[52] U.S. Cl. ...................... 252/48.6; 44/66; 260/399
[58] Field of Search ............. 252/48.6; 44/66; 260/399

[56] References Cited

U.S. PATENT DOCUMENTS

| | | | |
|---|---|---|---|
| 2,311,929 | 2/1943 | Chenicek et al. | 44/66 |
| 3,455,896 | 7/1969 | Den Herder et al. | 252/48.6 X |
| 3,740,333 | 6/1973 | Hutchinson et al. | 252/48.6 |
| 3,850,825 | 11/1974 | Vienna et al. | 252/48.6 |
| 4,134,845 | 1/1979 | Wakim | 252/48.6 |

Primary Examiner—W. J. Shine
Attorney, Agent, or Firm—Philip Hill

[57] ABSTRACT

Improved lubricant additive compositions, derived from fatty oils, comprise triglycerides which have been transesterified with polybasic carboxylic acids prior to sulfurization. Such additive compositions possess improved solubility in oils and impart improved lubrication properties to both lubricant and fuel compositions.

41 Claims, No Drawings

SULFURIZED, TRANSESTERIFIED OIL ADDITIVES AND THEIR USE IN A LUBRICATING OIL AND A FUEL

BACKGROUND OF THE INVENTION

It has been common practice to include in lubricant formulations additives to provide improved antiwear and rust inhibition properties. In the past, sulfurized triglycerides, such as sulfurized lard oil, have been utilized, especially in association with lightly refined aromatic mineral oils which provided sufficient solubility for the sulfurized triglycerides.

With the increased concern for toxicity of aromatic compounds found in such mineral oils, lubricant formulations now comprise essentially non-aromatic oils. This change to substantially non-aromatic base oils created a major problem, resulting from a significant decrease in solubility of the sulfurized triglycerides in the non-aromatic mineral oil, resulting in solidification and/or dropout of the sulfurized triglycerides.

While the solubility problem has been overcome, the modified lubricant products have been found to be either deficient in desirable lubricant properties or incapable of providing needed improvement in these properties.

In a typical approach to this problem, as reported in U.S. Pat. No. 3,455,896, sulfurized, low molecular weight polybutenes were reacted with liquid triglycerides, which were susceptible of sulfurization, to yield an additive. In U.S. Pat. No. 3,850,825, another additive was prepared by the sulfurization of a mixture of prime burning lard oil and alkyl oleate. In U.S. Pat. No. 3,740,333, $C_{10}$–$C_{16}$ alcohol esters of unsaturated fatty acids, having 18 to 22 carbon atoms, were blended with a triglyceride and either used "as is" or sulfurized. Modifications of such compositions have been reported in U.S. Pat. Nos. 4,149,982, 4,166,795, 4,166,796, 4,166,797 and 4,188,300. The use of polymer acids in modified triglycerides for use in soluble oils (aqueous dispersions) has been reported in U.S. Pat. No. 4,067,817.

Although these prior art efforts have increased the solubility of sulfurized fatty oils to acceptable values, there has remained a serious need for sulfurized additives possessing both good solubility and a combination of improved lubricant properties, such as, for example, better low temperature flow properties, better load carrying and antifriction properties, and a lack of sludging. Such improved lubricant properties would also be attractive for use in various fuels systems employed for power generation and heating purposes.

SUMMARY OF THE INVENTION

This invention relates to improved lubricant additive compositions comprising sulfurized fatty oils, to the process for their preparation, and to oil product compositions, including both fuels and lubricants, incorporating such sulfurized fatty oils. The additive compositions of this invention exhibit highly desirable solubility properties when employed in either lubricant or fuel formulations. The particularly desirable utility of these additive compositions derives from their providing generally improved performance characteristics, ranging from improved load carrying, antiwear, and friction properties, to reduced levels of deposits and varnish, and to improved pour-point depression.

This invention particularly relates to sulfurized, triglyceride additive compositions, comprising a sulfurized, transesterified triglyceride wherein the total acid component of the triglyceride includes from about 5 to about 50 mole % polybasic carboxylic acids.

This invention further relates to the method for preparation of such transesterified and sulfurized triglycerides.

This invention additionally relates to lubricant and fuel compositions incorporating such sulfurized, fatty oil additives, whereby improved performance in conventional usages is achieved. The additives of this invention may be employed in concentrations up to about 15 wt. % in lubricant formulations, including either mineral or synthetic oils, and up to about 0.1 wt. % in fuel compositions.

DESCRIPTION OF THE INVENTION

This invention is directed to additive compositions of sulfurized fatty oils, and to the process of preparing said compositions, which exhibit the required solubility properties in non-aromatic base oils or in synthetic base oils without the disadvantages associated with the prior art lubricant additive formulations. In addition, the compositions of this invention exhibit improved performance characteristics, over the compositions of the prior art, including improved load carrying, antiwear, and friction properties, reduced levels of deposits and varnish in used oils, and better pour-point depression. This invention is likewise directed to lubricant and fuel formulations which include the inventive additive compositions.

Triglycerides of the prior art, typically derived from plants and animals, do not provide maximum effectiveness as lubricant additives because of the chain length and/or the degree of unsaturation of the acid moiety. Modification of said acid moieties of the triglycerides, by transesterification, produces novel triglycerides that optimize the properties of the resulting additive when said novel triglycerides are coupled, through sulfur bonds, with solubilizing components, such as esters and/or olefins.

The acid moiety of the triglycerides components of the additives of this invention consists of an acid mixture including from 5 to about 50 mole % polybasic carboxylic acids. Such polybasic carboxylic acids include dibasic acids, having three or more carbon atoms, including saturated acids such as succinic, adipic, and azdaic acids, as well as unsaturated acids, such as dimers or co-monomers of unsaturated carboxylic acids. Preferred examples of the latter include dimers of oleic acid or linoleic acid and the coproduct of linoleic acid with acrylic acid or other short-chain unsaturated monocarboxylic acid. Other preferred unsaturated acids include trimers of linoleic and/or related acids. The unsaturated dibasic acids employed in this invention preferably have from about 21 to about 36 carbon atoms per molecule. The unsaturated tribasic acids generally will have about 54 carbon atoms per molecule. It is often advantageous to employ mixtures of the described acids and some such mixtures are readily available in commerce.

The transesterification reaction is carried out on blends of (1) triglycerides, (2) triglycerides and organic acids, or (3) triglycerides and esters of organic acids. Where acids are included in the reaction and the amount of free acids present in the transesterified blend is greater than about 15%, then the free acid is preferably esterified with monoalcohols, glycols or glycerol to decrease the free acid content prior to the subsequent sulfurization reaction. The esterification of free acids may also be effected when the concentration thereof is less than about 15% but this is not imperative.

Following the transesterification, or esterification, the reaction components are coupled by reaction with sulfur with, where desired, the added presence of solubilizing components, such as esters, olefins containing from about 8 to about 20 carbon atoms or blends thereof. The sulfurization is conducted in accordance with known procedures which generally consist of heating the mixture with elemental sulfur at temperatures from about 300° F. to about 400° F. for from about 1 to about 8 hours. The sulfur content of the additives of this invention should be within the range from about 2 to about 10 wt. %.

The additives of the present invention preferably utilize as starting compounds naturally occuring triglycerides. The compositions of such triglycerides are detailed in Bailey's *Industrial Oil and Fat Products*, Vol. I, 4th Edition, John Wiley and Sons.

A triglyceride is the ester product of glycerol and one or more fatty acids, represented schematically as

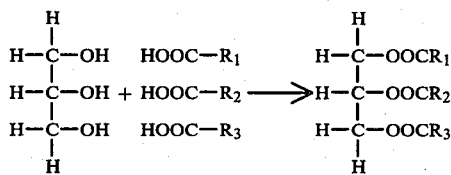

where $R_1$, $R_2$ and $R_3$ represent hydrocarbon groups which may be identical or different in chain length and may also be saturated or unsaturated.

Triglycerides from fish and animal oils contain acids with chain lengths that normally exceed 15 carbon atoms and usually contain large amounts of mono- and poly-unsaturated acids. Triglycerides from some plant species contain appreciable amounts of shorter chain acids, having 10, 12 or 14 carbon atoms. These shorter chain plant-derived acids tend to be mainly saturated acids.

In the process of preparing the triglyceride components of the additive of the present invention, commercially available triglycerides which do not have the required distribution of acids are transesterified with acids, esters or triglycerides having a higher proportion of the required distribution of acids. The resultant mixtures, following the transesterification, have the required average distribution of acids, preferably as triglycerides. Free acids in the transesterification reaction product may then be esterified with mono-alcohols, ranging from methyl to $C_{20}$, or with poly-alcohols, such as a glycol or glycerol. If the free acid content in the transesterification reaction product is greater than about 15%, esterification is a highly preferred procedure, whereas below the 15 % level esterification is optional. Transesterification is preferably carried out in the presence of a strong acid catalyst, at temperatures within the range from about 400° F. to about 450° F. for from about 1 to about 8 hours.

Prior to sulfurization, the transesterified mixture may be blended with a solubilizing component when further improved solubility is desired. Whenever there is a sufficient amount of free unsaturated acid in the transesterification reaction product, the esterification of such acids can provide the solubilizing factor. Otherwise additional solubilizing components, such as unsaturated esters or olefins are added prior to sulfurization.

Although the amount of solubilization component present, prior to sulfurization may, if desired, be as high as about 70 wt. %, such solubilization components, when employed, are preferably present in an amount within the range from about 5 wt. % to about 55 wt. %.

Transesterification catalysts are normally utilized to speed the reaction, although the reaction will proceed without a catalyst. The amount and type of catalyst can be widely varied. Known transesterification catalysts are tetrabutyl titanate, zinc acetate, sodium carbonate, sodium hydroxides, potassium hydroxide, sodium methylate, sodium sulfate, stannous oxalate, p-toluenesulfonic acid (PTSA), methanesulfonic acid (MSA), butylchlorotin dihydroxide, sulfuric acid, phosphoric acid and the like. p-Toluene-sulfonic acid and methanesulfonic acid are the preferred catalyst. The amount of catalyst utilized is in the range of about 0.01 wt. % to about 1 wt. % with the preferred range being about 0.03 wt. % to 0.5 wt. %.

During the transesterification reaction the presence of 0.15 to 1.0 wt. % water increases the rate of transesterification. However, during subsequent esterification it is desirable that the water that had been added, or is generated by the esterification reaction, be removed as promptly as possible, in order to drive the reaction to completion and thus increase the yield.

The following examples serve, without limitation, to describe the invention more fully as it relates to lubricant additive compositions. In the examples all parts and percentages are on a weight basis unless otherwise indicated.

In the following examples HOE alcohol refers to an 11 to 22 carbon alkyl alcohol, averaging about 16 carbons, mainly branched primary alcohol, sold commercially as Heavy Oxo Ends. Various acid reactants are more fully described in the particular examples.

EXAMPLE 1

A blend of 29 parts of a dimer acid, containing 73% dimerized linoleic/oleic acid, 24% trimerized linoleic-/oleic acid, and 3% monomer acids; and 43 parts of a solid triglyceride, having a melting point of about 100° F., (1:1 mole ratio) was heated at 400°–420° F. for 4 hours in the presence of 0.3 wt. % methanesulfonic acid. The acid value (A.V.) of the transesterified product was 68. Acid value is determined by titration (A.O.C.S. method Cd3a-63) and is defined as the number of milligrams of potassium hydroxide necessary to neutralize the free acids in one gram of sample.

To the transesterified product was added 28 parts HOE alcohol, and heating was continued at 400°–440° F. for 5 hours. The A.V. of the resulting product I was reduced by this process to 10.

Product I was then sulfurized by heating with elemental sulfur at 360°–370° F. for 3 hours, followed by cooling below 330° F. and passing air through the mixture for about 1.5 hours to remove $H_2S$ and other noxious light ends. The resultant product II contained 5.0 wt. % bound sulfur.

EXAMPLE 2

A blend of 16 parts dibasic acid, comprising the addition product of acrylic acid and conjugated linoleic acid, and 56 parts of the solid triglyceride (0.63:1 mole ratio) was heated as in Example 1. The A.V. was 58. Following additional heating with 28 parts HOE alcohol for 12 hours, the A.V. of product III decreased to 7. Sulfurization as in Example I gave product IV, having 5.7 wt. % bound sulfur.

EXAMPLE 3

The procedure of Example 1 was repeated employing 19 parts dibasic acid and 43 parts solid triglyceride (1:1 mole ratio). The A.V. was 87. After heating as in Example 1 with 38 parts HOE alcohol the A.V. of product V was 12. Sulfurization as in Example 1 yielded product VI, having 5 wt. % bound sulfur.

EXAMPLE 4

A blend of 19 parts of the dibasic acid and 38 parts HOE alcohol was heated at 340°–380° F. for 8 hours in the presence of 0.1 wt. % tetrabutyl titanate. The A.V. was 11. After sulfurizing in the presence of 43 parts solid triglyceride, product VII contained 5.0 wt. % bound sulfur.

EXAMPLE 5

The procedure of Example 1 was repeated employing 30 parts dibasic acid, 65 parts solid triglyceride, and 5 parts glycerol. After sulfurization, the product VIII contained 5 wt. % bound sulfur.

EXAMPLE 6

The procedure of Example 1 was repeated employing 29 parts of a trimer acid, containing 90% trimerized linoleic/oleic acid and 10% dimerized linoleic/oleic acid, and 43 parts of the solid triglyceride (0.67:1.0 mole ratio), and finally 28 parts HOE alcohol. The A.V. of the product IX was reduced from 65 to 9. After sulfurization, the product X contained 4.5 wt. % bound sulfur.

EXAMPLE 7

The procedure of Example 1 was repeated employing 12 parts of mixed dibasic acids, typically comprising 34% dodecanedioic, 40% undecanedioic, 7% sebacic, together with miscellaneous dibasic acids, 50 parts solid triglyceride, and 38 parts HOE alcohol. The A.V. of product XI was reduced from 88 to 9. After sulfurization, the product XII contained 5.1 wt. % bound sulfur.

EXAMPLE 8

The procedure of Example 1 was repeated employing 11 parts azelaic acid, 52 parts solid triglyceride, and 37 parts HOE alcohol. The A.V. of product XIII was reduced from 102 to 9. After sulfurization, the product XIV contained 4.3 wt. % bound sulfur.

EXAMPLE 9

The procedure of Example 1 was repeated employing 9 parts adipic acid, 53 parts solid triglyceride, and 38 parts HOE alcohol. The product XV had an A.V. of 10. The sulfurized product XVI contained 5.3 wt. % bound sulfur.

EXAMPLE 10

The procedure of Example 2 was repeated employing 9.7 parts dibasic acid and 80.3 parts solid triglyceride (0.3:1.0 mole ratio). The A.V. was 41. After heating with 20 parts HOE alcohol, the A.V. of product XVII was reduced to 10. After sulfurization, product XVIII contained 8.0 wt. % bound sulfur.

EXAMPLE 11

The procedure of Example 2 was repeated employing 17 parts of the dibasic acid, 59 parts of the solid triglyceride, and 24 parts of isodecyl alcohol. The product XIX has an A.V. of 12. After sulfurization, product XX contained 6.0 wt. % bound sulfur.

The following products were prepared for comparison purposes.

EXAMPLE A

A mixture of 88% prime burning lard oil and 12% methyl oleate was sulfurized to produce product A, containing 9.7% bound sulfur.

EXAMPLE B

A mixture of 55% prime burning lard oil and 45% HOE alcohol ester of tall oil fatty acids was sulfurized to yield sulfurized product B, containing 9.0% bound sulfur and having an A.V. of 9.

EXAMPLE C

A mixture of 50% prime burning lard oil and 50% isodecyl alcohol ester of tall oil fatty acids was sulfurized to yield product C, containing 9.1% bound sulfur and having an A.V. of 8.

Products exemplary of the sulfurized fatty oil additive compositions of this invention, prepared as described in Examples 1–11, above, together with comparison products A, B and C, were tested by conventional procedures at various concentration levels, ranging from 2 to 4 wt. %, in a mineral oil and in a commercially available engine oil, to determine the respective effects on flow properties. Results are presented in Tables I and II.

The mineral oil contained no pour depressant additive and did not flow at temperatures below 0° F. The engine oil contained pour depressants and still flowed at −22° F. Solubility of the products of this invention in these oils was good.

Table I shows clearly that the additives of this invention have excellent properties as pour depressants, keeping the oil fluid at lower temperatures when added to a mineral oil having a poor point of 0° F.

Table II shows that sulfurized fatty oils (Products A, B and C) diminish the low temperature flow properties of the pour-depressed engine oil. However, additives of the present invention can generally be used at higher concentrations without any harmful effect upon the flow properties of the same engine oils.

The improved load carrying and friction reduction properties imparted by the use of the additives of the present invention are illustrated by the data in Tables III and IV, showing the improved load carrying and friction reduction (torque) as measured by the Falex step-up test. Tests presented in Table III were conducted with the pour-depressed engine oil. Tests presented in Table IV illustrate the additive performance with non-formulated base oils, including a mineral oil and a synthetic lubricating oil base stock.

Falex procedures for evaluating lubricants are described in Lubrication Engineering, 24, No. 8, 349–358 (1968). The procedure employed in these tests was as follows:

After a 5 minute warmup at 250 lbs., the load is increased in 250 lb. increments and held at each increment for one minute, until failure, which is of the weld type.

Torque comparisons were also made to show differences in friction.

Crankcase oil, formulated to be a high quality SE Grade 10W40 crankcase oil, was evaluated using a four-ball machine in testing for friction and wear as described in the ASTM-D-2266 procedure. The crankcase oil alone was compared with crankcase oil containing 2% additive B or 2% additive II. Tests were conducted at 1800 R.P.M., using a 40 kg. load, for one hour at 350° F. The results obtained were as follows:

| Additives | Wear-Scar Diameter |
|---|---|
| Crankcase Oil | 0.98 mm. |
| +2% Additive B | 0.80 mm. |
| + 2% Additive II | 0.65 mm. |

Several products were tested for solubility in synthetic hydrocarbon oils by dissolving in Gulf Synlube 4cs with warming and stirring. The solutions were then kept at 40° F. for 3 days and finally observed after warming to room temperature. The observed results were:

| 2% A | Heavy Bottom Layer |
|---|---|
| 2% B | Slight dropout |
| 2% C | Slight dropout |
| 2% I | Clear |
| 2% II | Hazy |
| 2% IV | Hazy, slight dropout |
| 2% VI | Hazy |
| 2% IX | Clear |
| 2% X | Hazy, slight dropout |

The sulfurized fatty oil additive compositions of this invention are effective when employed in lubricating oils at concentrations ranging from about 0.05 to about 15 wt. %. The preferred concentration range is generally from about 0.5 to about 5 wt. %.

In other embodiments of this invention the sulfurized fatty oil additive compositions are effective in various types of fuels, particularly to improve the lubrication of fuel pumps; to reduce wear on pistons, rings, and cylinders; and to reduce deposit formation. Such fuels broadly include gasolines, for use in spark-ignition internal combustion engines; diesel oils, for use in compression-ignition internal combustion engines; and heating (or furnace) oils, for use in oil-fired burner assemblies. Other advantages include, when employed in fuel oils or diesel fuels, reduction of pour points and attendant reduction in plugging of oil filters. In such novel and improved fuel compositions, the additives of this invention are effective at relatively low concentrations within the range from about 0.0005 to about 0.1 wt. %, and preferably from about 0.0015 to about 0.05 wt. %.

TABLLE I

Low Temperature Flow of a Mineral Oil[1]
(viscosity 27 cst. at 40° C.)
After 16 Hours at −20° F.

| Additive | 2% | 3% |
|---|---|---|
| A | No Flows | — |
| B | Flows | No Flow |
| C | Flows | No Flow |
| II | Flows | Flows |
| VI | Flows | Flows |

[1]Without additives, no flow at 0° F.

TABLE II

Commercial 10W40 Oil "Brand A"[1]
After 16 Hours at −22° F.

| Additive | 2% | 3% | 4% |
|---|---|---|---|
| A | No Flow | — | — |
| B | Flows[2] | No Flow | — |
| C | Flows[2] | No Flow | — |
| II | Flows | Flows | — |
| IV | Flows | Flows | Flows |
| VI | Flows | Flows | Flows |
| VII | Flows | No Flows | — |
| X | Flows | Flows | — |
| XII | Flows | No Flow | — |
| XIV | Flows | Flows | — |
| XVI | Flows | Flows | — |
| XVIII | Flows | No Flow | — |

[1]Without additives, flows at −22° F.
[2]Marginal Flow

TABLE III

Falex Step-Up Test, 10W40 Oil, "Brand A"

| | Lbs. Load Before Failure | Torque at 1500 lbs. |
|---|---|---|
| Oil alone | 1250 | (45 at 1250) |
| 2% B | 1500 | 30 |
| 2% C | 1500 | 30 |
| 2% II | 2000 | 25 |
| 3% II | 2000 | 28 |
| 2% IV | 2250 | 25 |
| 3% IV | 2250 | 25 |
| 2% VI | 2250–2500 | 25 |
| 3% VI | 3000 | 26 |
| 2% VII | 1500 | 30 |
| 3% VII | 1500 | 28 |
| 2% X | 1750 | 25 |
| 3% X | 2000 | 25 |
| 2% XII | 1750 | 25 |
| 3% XII | 1750–2000 | 24 |
| 2% XIV | 1500 | 35 |
| 3% XIV | 1750 | 26 |
| 2% XVI | 1500–1750 | 28 |
| 3% XVI | 1750 | 28 |
| 2% XVIII | 1500 | 27 |
| 3% XVIII | 2000 | 26 |
| 3% XX | 2250 | 23 |

TABLE IV

Falex Step-Up Test in Non-Formulated Base Hydrocarbons

| | Lbs. Load Before Failure | Torque at 1250 |
|---|---|---|
| Mid-Continent Oil | 750 | — |
| Oil + 2% II | 1250 | — |
| Oil + 2% VI | 1250 | — |
| Gulf Synfluid 4cs | 250–500 | — |
| Gulf Synfluid 4cs | | |
| + 2% I | 1000–1250 | — |
| + 2% II | 1500 | 21 |
| + 2% VI | 1500 | 22 |
| + 2% IX | 1000–1250 | — |

What is claimed is:

1. A sulfurized, triglyceride additive composition comprising a sulfurized, transesterified triglyceride wherein the total acid component of the triglyceride includes from about 5 to about 50 mole % polybasic carboxylic acids.

2. The composition of claim 1 wherein the polybasic carboxylic acids comprise dibasic acids having from about 3 to about 36 carbon atoms per molecule.

3. The composition of claim 2 wherein the dibasic acids comprise unsaturated acids having from about 21 to about 36 carbon atoms.

4. The composition of claim 3 wherein the unsaturated dibasic acids comprise dimerized linoleic acid.

5. The composition of claim 3 wherein the unsaturated dibasic acids comprise the dimerized product of linoleic and acrylic acids.

6. The composition of claim 1 wherein the polybasic carboxylic acids comprise a mixture of dibasic and tribasic acids having from about 3 to about 54 carbon atoms per molecule.

7. The composition of claim 6 wherein the mixture of dibasic and tribasic acids comprises unsaturated acids having from about 21 to about 54 carbon atoms.

8. The composition of claim 7 wherein the mixture of unsaturated dibasic and tribasic acids comprises dimers and trimers of linoleic acid.

9. The composition of claim 1, additionally comprising a solubilization agent.

10. The composition of claim 9 wherein the solubilization agent is selected from the group consisting of triglycerides, olefins, esters of unsaturated carboxylic acids, and mixtures thereof.

11. The composition of claim 10 wherein the solubilization agent is a triglyceride.

12. The composition of claim 10 wherein the solubilization agent is an olefin.

13. The composition of claim 12 wherein the olefin contains from about 8 to about 20 carbon atoms, alone or in mixtures thereof.

14. The composition of claim 10 wherein the solubilization agent is an ester of an unsaturated carboxylic acid.

15. The composition of claim 9 wherein the solubilization agent is present in an amount within the range from about 5 wt. % to about 70 wt. %, based on the sulfurized, transesterified triglyceride.

16. The composition of claim 15 wherein the solubilization agent is present in an amount within the range from about 5 wt. % to about 55 wt. %, based on the sulfurized, transesterified triglyceride.

17. The composition of claim 1 wherein bound sulfur is present in an amount within the range from about 2 wt. % to about 10 wt. %, based on the sulfurized, transesterified triglyceride.

18. A process for preparing a sulfurized, transesterified triglyceride additive composition, comprising the steps of:
  (1) transesterifying one or more triglycerides with one or more organic polybasic acids, or esters thereof, to yield a transesterified triglyceride wherein the total acid component comprises from about 5 mole % to about 50 mole % polybasic carboxylic acids; and
  (2) sulfurizing the transesterified triglyceride product mixture of step 1 with elemental sulfur to incorporate bound sulfur in an amount within the range from about 2 wt. % to about 10 wt. %, based upon the transesterified triglyceride product mixture.

19. The process of claim 18, wherein said polybasic carboxylic acids comprise dibasic acids having from about 3 to about 36 carbon atoms per molecule.

20. The process of claim 19, wherein said dibasic acids comprise unsaturated acids having from about 21 to about 36 carbon atoms.

21. The process of claim 20, wherein said unsaturated dibasic acids comprise dimerized linoleic acid.

22. The process of claim 20, wherein said unsaturated dibasic acids comprise the dimerized product of linoleic and acrylic acids.

23. The process of claim 18, wherein said polybasic carboxylic acids comprise a mixture of dibasic and tribasic acids having from about 3 to about 54 carbon atoms per molecule.

24. The process of claim 23, wherein said mixture of dibasic and tribasic acids comprises unsaturated acids having from about 21 to about 54 carbon atoms.

25. The process of claim 24, wherein said mixture of unsaturated dibasic and tribasic acids comprises dimers and trimers of linoleic acid.

26. The process of claim 18, additionally comprising the step of esterifying free acids in the transesterification reaction product with an alcohol component prior to the sulfurization step.

27. The process of claim 26 wherein said alcohol component for esterification comprises branched chain aliphatic primary alcohols.

28. The process of claim 18, additionally comprising the step of blending said transesterification reaction product with a compound selected from the group consisting of triglycerides, esterified fatty acids, α-olefins and mixtures thereof, prior to the sulfurization step.

29. The process of claim 18, wherein said transesterification step is carried out in the presence of a transesterification catalyst.

30. The process of claim 18, wherein said transesterification catalyst is selected from the group consisting of tetrabutyl titanate, zinc acetate, sodium carbonate, sodium sulfate, stannous oxalate, p-toluenesulfonic acid, methanesulfonic acid, sulfuric acid, butylchlorotin dihydroxide, and phosphoric acid.

31. The process of claim 29, wherein said transesterification catalyst is present in an amount within the range from about 0.01 to about 1 wt. %, based on the triglycerides.

32. The process of claim 31, wherein said catalyst is present in an amount within the range from about 0.03 to about 0.5 wt. %.

33. The process of claim 30 wherein said catalyst is p-toluenesulfonic acid.

34. The process of claim 30, wherein said catalyst is methanesulfonic acid.

35. A lubricating oil composition, comprising:
  (1) a refined base oil, having lubricating oil viscosity and volatility properties; and
  (2) a minor amount, from about 0.05 to about 15 wt. % of the lubricating oil composition, of a sulfurized, triglyceride additive composition, comprising a sulfurized, transesterified triglyceride wherein the total acid component of the triglyceride includes from about 5 to about 50 mole % polybasic carboxylic acids.

36. The lubricating oil composition of claim 35 wherein the sulfurized triglyceride additive composition is present in an amount within the range from about 0.5 to about 5 wt. % of the lubricating oil composition.

37. A fuel composition, comprising:
  (1) a blended base fuel, having suitable volatility and combustion properties; and
  (2) a minor amount, from about 0.0005 to about 0.1 wt. % of the fuel composition, of a sulfurized triglyceride additive composition, comprising a sulfurized, transesterified triglyceride wherein the total acid component of the triglyceride includes from about 5 to about 50 mole % polybasic carboxylic acids.

38. The fuel composition of claim 37 wherein the blended base fuel is a gasoline fuel, for use in a spark-ignition internal combustion engine.

39. The fuel composition of claim 37 wherein the blended base fuel is a diesel fuel, for use in a compression-ignition internal combustion engine.

40. The fuel composition of claim 37 wherein the blended base fuel is a heating oil, for use in an oil-fired burner assembly.

41. The fuel composition of claim 37 wherein the sulfurized triglyceride additive composition is present in an amount within the range from about 0.0015 to about 0.05 wt. % of the fuel composition.

* * * * *